United States Patent [19]

Dumoulin et al.

[11] Patent Number: 5,133,357
[45] Date of Patent: Jul. 28, 1992

[54] QUANTITATIVE MEASUREMENT OF BLOOD FLOW USING CYLINDRICALLY LOCALIZED FOURIER VELOCITY ENCODING

[75] Inventors: Charles L. Dumoulin, Ballston Lake; Christopher J. Hardy, Schenectady, both of N.Y.; Steven P. Suza, Williamstown, Mass.; Stephen A. Ash, Iowa City, Iowa

[73] Assignee: General Electric Company, Schenectady, N.Y.

[21] Appl. No.: 651,872

[22] Filed: Feb. 7, 1991

[51] Int. Cl.$^5$ .............................................. A61B 5/055
[52] U.S. Cl. .................................. 128/653.3; 324/306; 324/309
[58] Field of Search ...................... 128/653.2, 653.3; 324/306, 307, 309, 300

[56] References Cited

U.S. PATENT DOCUMENTS

| | | | |
|---|---|---|---|
| 4,431,968 | 2/1984 | Edelstein | 324/309 |
| 4,782,839 | 11/1988 | Hennig et al. | 128/653.3 |
| 4,796,635 | 1/1989 | Dumoulin | 128/653 |
| 4,849,697 | 7/1989 | Cline et al. | 128/653.3 |
| 4,995,394 | 2/1991 | Cline et al. | 128/653.2 |

OTHER PUBLICATIONS

Dixon, W. Thomas; Du, Leila N.; Faul, David D.; Mokhtar, Gado; Rossnick, Susan. "Projection Angiograms of Blood Labeled by Adiabatic Fast Passage." *Magnetic Resonance in Medicine.* vol. 3, p. 454, 1986.

Nishimura, Dwight G.; Macovski, Albert; Paul, John M.; and Conolly, Steve M. "MR Angiography by Selective Inversion Recovery." *Magentic Resonance in Medicine.* vol. 4, p. 193, 1987.

Laub, G. A. and W. A. Kaiser. "MR Angiography with Gradient Motion Refocusing." *Journal of Computer Assisted Tomography.* vol. 3, p. 377, 1988.

Dumoulin, C. L.; Cline, H. E.; Souza, S. P.; Wagle, W. A.; Walker, M. F. "Three-Dimensional Time-of-Flight Magnetic Resonance Angiography Using Spin Saturation." *Magnetic Resonance in Medicine.* vol. 11, p. 35, 1989.

Keller, Paul J., Ph.D.; Drayer, Burton P., M.D.; Fram, Evan K., M.D.; Williams, Kenneth D., M.D.; Dumoulin, Charles L., Ph.D.; Souza, Steven P. Ph.D. "MR Angiography with Two Dimensional Acquisition and Three-Dimensional Display." *Radiology* 1989; 173:527.

Wedeen, Van J.; Meuli, Reto A.; Edelman, Robert R.; Geller, Stuart C.; Frank, Lawrence R.; Brady, Thomas J.; Rosen Bruce R. "Projective Imaging of Pulsatile Flow with Magnetic Resonance." *Science,* vol. 230, p. 946, 1985.

Dumoulin, D. L. and Hart, H. R. "Magnetic Resonance Angiography." *Radiology,* vol. 161, p. 717, 1986.

DuMoulin, C. L.; Cline, H. E.; Souza, S. P.; Hart, HR. "Rapid Scan Magnetic Resonance Angiography." *Mag-*

(List continued on next page.)

Primary Examiner—Lee S. Cohen
Assistant Examiner—K. M. Pfaffle
Attorney, Agent, or Firm—Lawrence P. Zale; James C. Davis, Jr.; Marvin Snyder

[57] ABSTRACT

A method of imaging and quantitatively measuring blood velocity distribution within a selected vessel employs Nuclear Magnetic Resonance cylindrical excitation of the sample to be imaged, followed by Fourier velocity encoding excitation along a second axis for selectively encoding molecules based upon their flow velocities, then sensing the re-radiated signal data acquired in the presence of a readout gradient to provide resolution along the cylindrical axis, and reconstructing a velocity profile. Spatial localization is accomplished with an excitation pulse having a cylindrical rather than slab geometry. This method can be combined with cardiac synchronization to measure flow dynamics or it can be applied without synchronization to measure steady flow. The geometry of the measurement is flexible in that the directions of flow sensitivity and geometric resolution are independent.

12 Claims, 20 Drawing Sheets

OTHER PUBLICATIONS

*netic Resonance in Medicine.* vol. 5, p. 238, 197.

Dumoulin, C. L.; Souza, S. P.; Walker, M. F.; Wagle, W. "Three-Dimensional Phase Contrast Angiography." *Magnetic Resonance in Medicine.* vol. 9, p. 139, 1989.

Masaryk, Thomas J., MD; Modic, M. T., MD; Ross, J. S., MD; Ruggieri, P. M., MD; Laub, G. A., PhD; et al. "Intracranial Circulation: Preliminary Clinical Results with Three-Dimensional (Volume) MR Angiography." *Radiology,* vol. 171, p. 793, 1989.

Masaryk, Thomas J., MD; Modic, M. T., MD; Ross, J. S., MD; Ruggeri, P. M., et al. "Three-Dimensional (Volume) Gradient-Echo Imaging of the Carotid Bifurcation: Preliminary Clinical Experience." *Radiology.* vol. 171, p. 801, 1989.

Wagle, William A.; Dumoulin, C. L.; Souza, S. P.; Cline, H. E. "3DFT Magnetic Resonance Angiography of Carotid Artery and Basilar Artery Disease." *American Journal of Neuroradiology.* vol. 10, p. 911, 1989.

Walker, M. F.; Souza, S. P.; Dumoulin, C. L. "Quantitative Flow Measurement in Phase Contrast MR Angiography." *Journal of Computer Assisted Tomography.* vol. 12, p. 304, 1988.

Nayler, G. L.; Firmin, D. N.; Longmore, D. B. "Blood Flow Imaging by Cine Magnetic Resonance." *Journal of Computer Assisted Tomography.* vol. 10, p. 715, 1986.

Wehrli, Felix W.; Shimakawa, Ann; MacFall, J. R.; Axel, Leon; Perman, William. "MR Imaging of Venous and Arterial Flow by a Selective Saturation-Recovery Spin Echo (SSRSE) Method." *Journal of Computer Assisted Tomography.* vol. 9, p. 537, 1985.

Edelman, Robert R.; Finn, J. P.; Wentz, Klause; Zhao, Bin; et al. "MR Angiography and Flow Quantitation in the Portal Venous System." *Proceedings of the 8th Annual Meeting of the Society of Magnetic Resonance in Medicine. Amsterdam,* p. 208, 1989.

Shimizu, Koji; Matsuda, Tetsuya; Sakurai, Tsunetaro; et al. "Visualization of Moving Fluid: Quantitative Analysis of Blood Flow Velocity Using MR Imaging." *Radiology.* vol. 159, p. 195, 1986.

Feinberg, David A.; Crooks, Lawrence E.; Sheldon, Phillip; et al. "Magnetic Resonance Imaging the Velocity Vector Components of Fluid Flow." *Magnetic Resonance in Medicine.* vol. 2, p. 555, 1985.

Hennig, Jurgen; Muri, Marcel; Brunner, Peter; Friedburg, Hartmut. "Quantitative Flow Measurement with the Fast Fourier Flow Technique." *Radiology.* vol. 166, p. 237, 1988.

Souza, S. P.; Steinberg, F. L.; Caro, C.; Dumoulin, E. K.; et al. *Proceedings of the 8th Annual Meeting of the Society of Magnetic Resonance in Medicine, Amsterdam.* p. 102, 1989.

Pauly, John; Nishimura, Dwight; Macovski, Albert. "A k-Space Analysis of Small-Tip-Angle Excitatin." *Journal of Magnetic Resonance.* vol, 81, p. 43, 1989.

Hardy, Christopher J.; Cline, Harvey E. "Broadband Nuclear Magnetic Resonance Pulses with Two-Dimensional Spatial Selectivity." *Journal of Applied Physics.* vol. 66, p. 1513, 1989.

Hardy, Christopher J.; Cline, Harvey E.; Bottomley, Paul A. "Correcting for Nonuniform k-Space Sampling in Two-Dimensional NMR Selective Excitation." *Journal of Magnetic Resonance.* vol. 87, p. 639, 1990.

Hardy, Christopher J.; Cline, Harvey E. "Spatial Localization in Two Dimensions Using NMR Designer Pulses." *Journal of Magnetic Resonance.* vol. 82, p. 647, 1989.

Dumoulin, C. L.; Souza, S. P.; Walker, M. F.; Yoshitome, E. "Time-Resolved Magnetic Resonance Angiography." *Magnetic Resonance in Medicine.* vol. 6, p. 275, 1988.

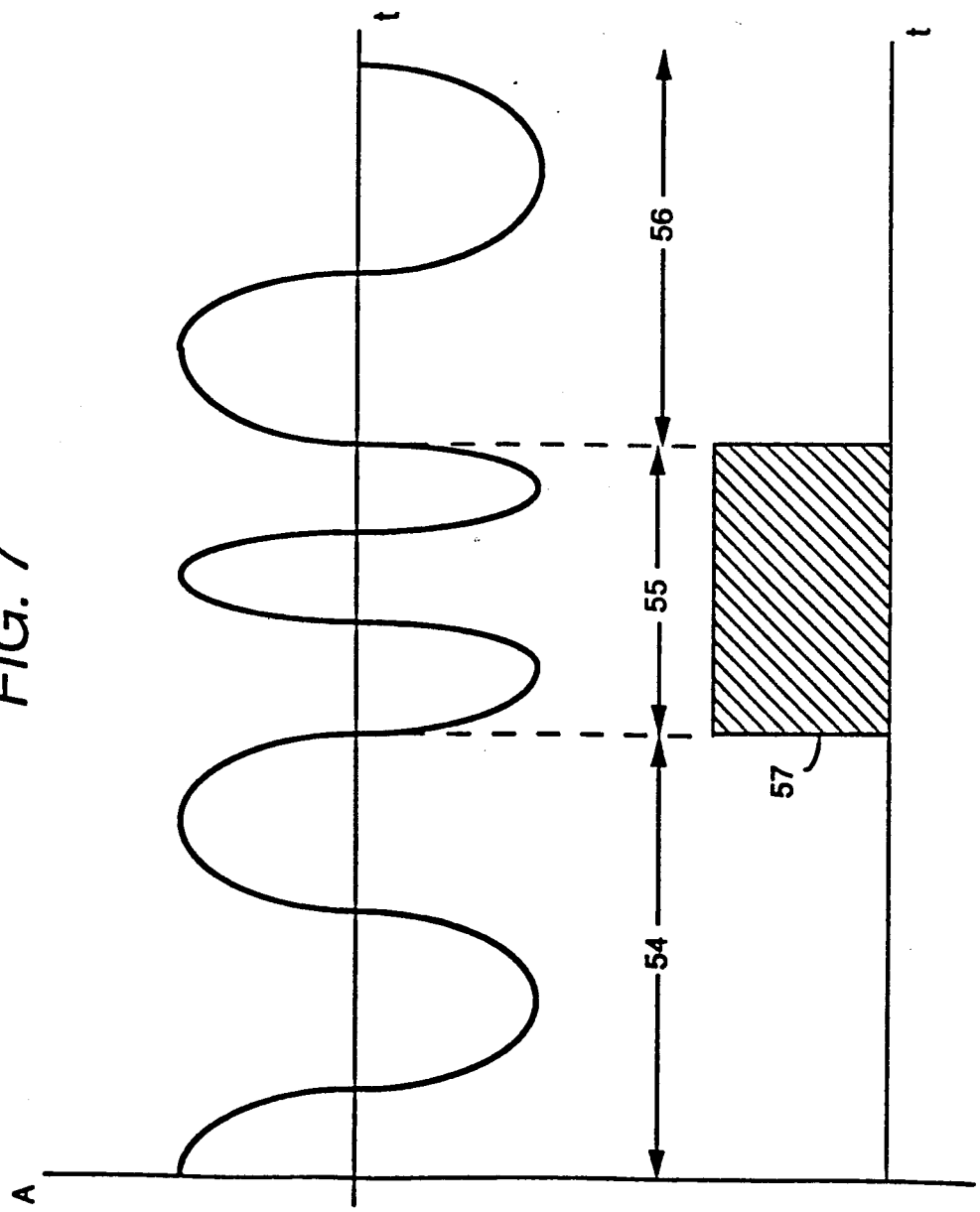

QUANTITATIVE MEASUREMENT OF BLOOD FLOW USING CYLINDRICALLY LOCALIZED FOURIER VELOCITY ENCODING

BACKGROUND OF THE INVENTION

1. Field of the Invention

This invention relates to quantitative measurement of blood flow, and more specifically, quantitative measurement of blood flow using Magnetic Resonance Imaging

2. Description of Related Art

Angiography, or the imaging of vascular systems by Magnetic Resonance (MR) has been demonstrated using a variety of techniques based on time-of-flight phenomena and the phenomena of velocity-induced phase shifts. See Dixon WT, Du L. N., Faul D. D., et al. "Projection Angiograms of Blood Labelled by Adiabatic Fast Passage" in *Magn. Reson. Med*, 3:454, 1986; Nishimura D. G., Macovski A., Pauly J. M., et al. "MR Angiography by Selective Inversion Recovery" in *Magn. Reson. Med*, 4:193, 1987; Laub G. A., Kaiser W. A. "MR Angiography with Gradient Motion Refocusing" in *J. Comp. Asst. Tomogr.*, 12:377, 1988; Dumoulin C. L., Cline H. E., Souza S. P., et al. "Three Dimensional Time-of-Flight Magnetic Resonance Angiography Using Spin Saturation" in *Magn. Reson. Med.*, 11:35, 1989; Keller P. J., Drayer B. P., Fram E. K., et al. "MR Angiography Via 2D-Acquisition, but Yielding a 3D-Display: A Work in Progress" in *Radiology*, 173:527 (1989); Wedeen V. J., Meuli R. A., Edelman R. R., et al. "Projective Imaging of Pulsatile Flow with Magnetic Resonance" in *Science*, 230:946, 1985; Dumoulin C. L., Hart H. R. "Magnetic Resonance Angiography" in *Radiology*, 161:717, 1986; Dumoulin CL, Souza S. P., Hart H. R. "Rapid Scan Magnetic Resonance Angiography" in *Magn. Reson. Med.*, 5:238, 1987; Dumoulin CL, Souza SP, Walker MF, et al. "Three Dimensional Phase Contrast Angiography" in *Magn. Reson. Med.*, 9:139, 1989.

Clinical use of several MR angiographic techniques in the head and neck have been recently reported See Masaryk T. J., Modic M. T., Ross J. S., et al. "Intracranial Circulation: Preliminary Clinical Results with Three-Dimensional (Volume) MR Angiography" in *Radiology*, 171:793, (1989); Masaryk T. J., Modic M. T., Ruggieri P. M., et al. "Three-Dimensional (Volume) Gradient-Echo Imaging of the Carotid Bifurcation: Preliminary Clinical Experience" in *Radiology*, 171:801,(1989); Wagle W. A., Dumoulin C. L., Souza S. P., et al. "3DFT Magnetic Resonance Angiography of Carotid artery and Basilar Artery Disease" in *Am. J. Neuroradiology*, 10:911 (1989).

Some degree of quantification has proven possible with some phase sensitive methods. See Walker M. F., Souza S. P. and Dumoulin C. L. "Quantitative Flow Measurements by Phase Contrast Magnetic Resonance Angiography" in *J. Comp. Asst. Tomogr.* 12:304 (1988); Nayler G. L., Firmin D. N. and Longmore D. B. "Blood Flow Imaging by Cine Magnetic Resonance" in *J. Comp. Asst. Tomogr.* 10:715 (1986).

While the above methods of MR angiography can provide excellent morphological detail, it is frequently difficult to obtain quantitative flow information. This is because a given volume element, called a volume pixel ("voxel") may contain a distribution of velocities which interfere with one another in the detection or data collection process.

Several non-angiographic techniques have been proposed though they are not common. For example, bolus tracking in which the bulk movement of excited spin magnetization is monitored, has been reported. This has been done with boluses of inverted spin magnetization. See Morse O. and Singer J. R. "Blood Velocity Measurements in Intact Subjects", *Science* 170:440 (1970). Boluses of saturated spin magnetization were described by Wehrli F. W., Shimakawa A., MacFall J. R., et al. "MR Imaging of Venous and Arterial Flow by a Selective Saturation-Recovery Spin Echo (SSRSE Method" in *J. Comp. Asst. Tomogr.* 9:537 (1985), Edelman RR, Finn J. P., Wentz K., et al. "Magnetic Resonance Angiography and Flow Quantitation in the Portal Venous System" in *Proceedings of the 8th Annual meeting of the Society of Magnetic Resonance in Medicine, Amsterdam*, 1899, 208. Boluses of transverse spin magnetization were also monitored by Shimizu K., Matsuda T., Sakurai T., et al. "Visualization of Moving Fluid: Quantitative Analysis of Blood Flow Velocity Using MR Imaging" in *Radiology*, 159:195 (1986). An alternative approach is the use of flow-encoding gradients which provide a motion-dependent phase shift as disclosed in Feinberg D. A., Crooks L. E., Sheldon P., et al. "Magnetic Resonance Imaging the Velocity Vector Components of Fluid Flow" in *Mag. Reson. Med.* 2:555 (1985); Hennig J., Muri M., Brunner P., et al. "Quantitative Flow Measurement with the Fast Fourier Flow Technique" in *Radiology*, 166:237 (1988); Souza S. P., Steinberg F. L., Caro C., et al. *Proceedings of the 8th Annual Meeting of the Society of Magnetic Resonance in Medicine, in Amsterdam*, 1989, pg. 102; Moran P. R. "A Flow Velocity Zeugmatographic Interlace for NMR Imaging in Humans" in *Mag. Reson. Imag.* 1:197, (1982).

Fourier-encoded velocity measurements proposed by Feinberg et al. and Hennig et al. employ a spin-warp imaging pulse sequence which uses flow sensitive phase-encoding gradient pulses to quantify velocity.

Feinberg et al. and Hennig et al. provide a spatial representation of the velocity of flowing blood, but in only a single dimension. There is a need to provide a noninvasive method of determining the flow of fluids in selected vessels which is accurate and reliable.

In addition, fluid flow measurements are a good indication of hemodynamic properties of a given vessel. These hemodynamic properties are important in Medical Applications such as in diagnosing a variety of abnormalities and diseases. It would be useful to be able to acquire the hemodynamic properties without the use of invasive techniques.

SUMMARY OF THE INVENTION

The present invention provides a more selective method of measuring fluid flow through use of MR imaging than heretofore attainable. The method provides for quantitative measurement of fluid flow by applying a homogeneous magnetic field over the subject to be imaged and performing a plurality of magnetic resonance scans, followed by reconstruction of the data to calculate the flow velocities of the fluid. The scan is executed by first applying a cylindrical NMR excitation to the portion of the subject which is to be imaged. Next, a flow encoding magnetic field gradient is applied along the direction in which flow is to be measured. Finally, data are collected by use of an antenna sensing the NMR signal which is re-radiated from the subject and stored for future reconstruction.

Cylindrical NMR excitation of the subject is accomplished by simultaneous application of two mutually orthogonal time-changing magnetic field gradients accompanied by an rf pulse of a predetermined amplitude and duration.

Once the cylindrical field, or "excitation cylinder" has been established, flow encoding can take place The scan is repeated many times, with the flow encoding magnetic gradient having a constant predetermined amplitude for each scan, but differing in amplitude for successive scans. In order to encode velocity of the fluid, the flow encoding magnetic gradient pulse will have two lobes, each lobe having the same area under an amplitude versus duration curve, but having opposite polarities.

After the cylindrical field is excited and the velocity is encoded, a bipolar magnetic readout gradient is applied parallel to the axis of the excitation cylinder. An antenna senses the amount of rf signal re-radiated by the excitation cylinder. These rf signal data are stored, and the entire scan is repeated for another amplitude value of the flow-encoded magnetic gradient Once all the data are acquired, a two dimensional Fourier transform of the scan data is performed to reconstruct the fluid velocity profile. The fluid velocity profile, combined with the cross sectional diameter of a vessel to be imaged, can be used to calculate the fluid flow through the vessel.

OBJECTS OF THE INVENTION

It is an object of the invention to provide an improved method of NMR imaging of fluid flow in living subjects in which an accurate quantitative measurement of the flow can be calculated. It is another object of the invention to provide a method of NMR imaging such that materials having motion will be imaged and those having no motion will be suppressed.

It is another object of the invention to provide NMR imaging of nuclei described by second order differentials of motion or higher order differentials of motion and suppressing images of those nuclei described by first order differentials of motion or no motion.

BRIEF DESCRIPTION OF THE DRAWINGS

The features of the invention believed to be novel are set forth with particularity in the appended claims. The invention itself, however, both as to organization and method of operation, together with further objects and advantages thereof, may best be understood by reference to the following description taken in conjunction with the accompanying drawings(s) in which:

FIG. 7 is a graph of amplitude of the transverse magnetization vector versus time, upon application of a magnetic field gradient pulse.

DETAILED DESCRIPTION OF THE PREFERRED EMBODIMENT

U.S. Pat. Nos. 4,431,968, Edelstein et al., issued Feb. 14, 1984; 4,706,024, Dumoulin, issued Nov. 10, 1987; and 4,796,635, Dumoulin, issued Jan. 10, 1989, all of which are assigned to the present assignee, are hereby incorporated by reference and made part of this disclosure.

Figure 1:
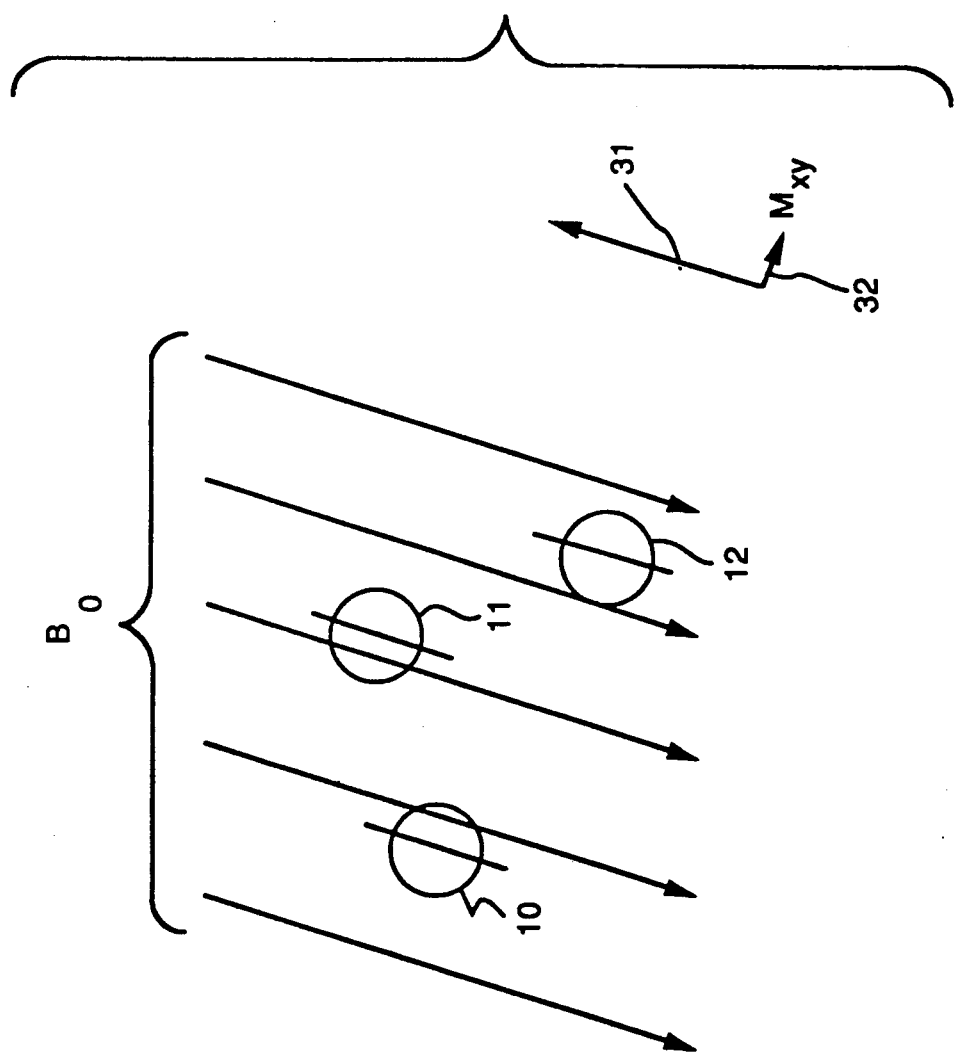
FIG. 1 is a representation of transverse and longitudinal magnetization of spins in a static magnetic field.

Free unpaired spinning protons in the nucleus of a molecule, ("spins"), normally hydrogen nuclei 10, 11 and 12 as shown in FIG. 1, align themselves in a magnetic field $B_0$ such that their axes precess about the magnetic field Spins 10, 11 and 12 represent a sample of the population of spins in a given sample Since there is a population of spins, the macroscopic total of aligned spins cause a net longitudinal magnetization 31 along the magnetic field $B_0$. The net sum of the total population 10, 11 and 12 also results in a small transverse magnetization ("$M_{xy}$") 32. The net transverse magnetization 32 can be increased by forcing spins 10, 11 and 12 out of alignment with magnetic field $B_O$ by a force applied by a tuned radio frequency (rf) pulse, or by an external magnetic field. Thus an rf pulse applied in the presence of a magnetic field of predefined strength causes excitation or resonance of the spins, increasing transverse magnetization of the spins as represented by spins 14, 15, and 16 of FIG. 2.

It is possible, by choosing the strengths of the rf pulse and magnetic field gradients, to selectively choose spins for excitation. Spatial localization of spins can be performed by choosing the rf pulse and magnetic field gradients to excite spins of a specific desired area of the subject to be imaged.

Figure 3:
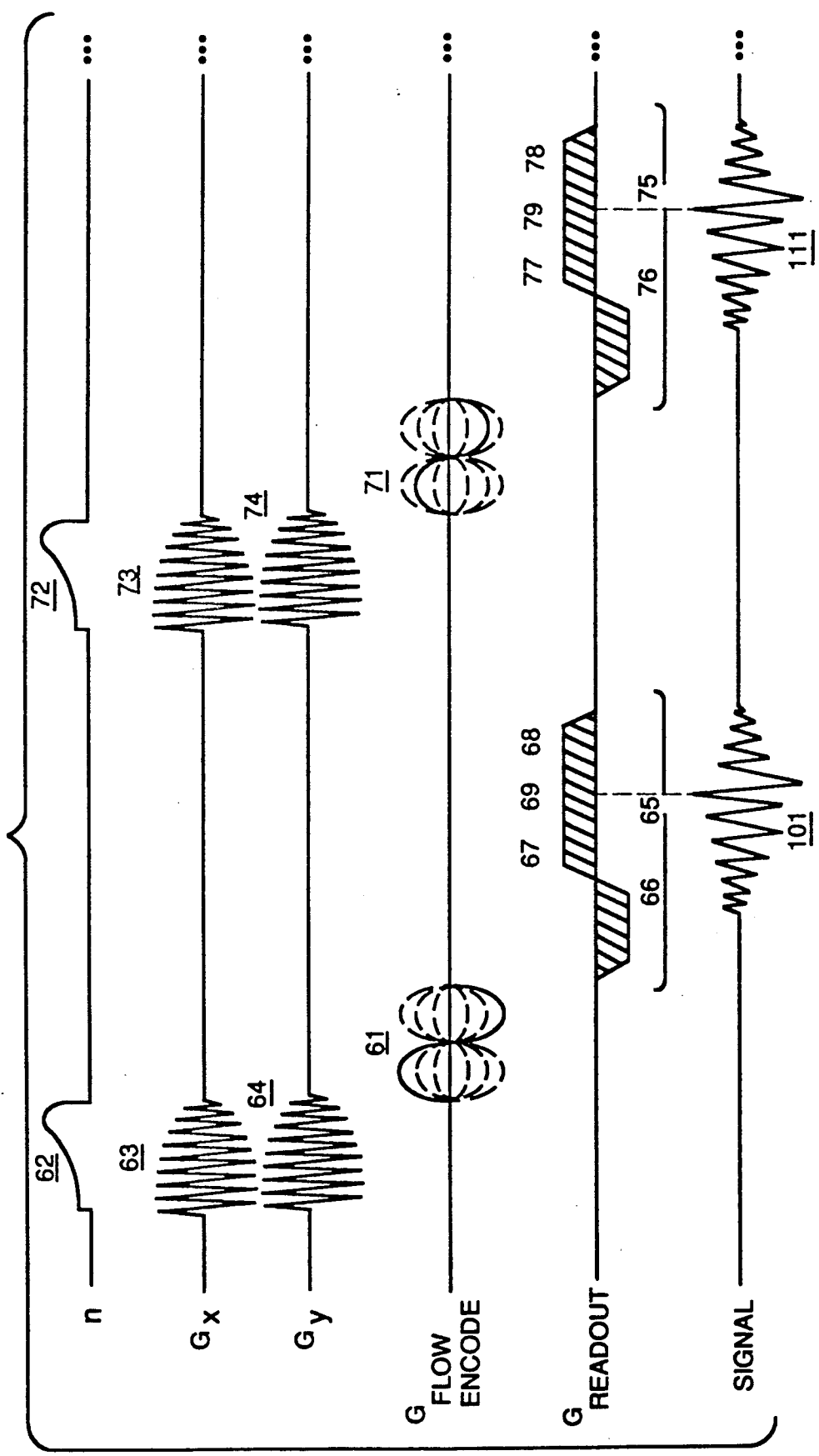
FIG. 3 is a time vs. amplitude diagram of the pulse sequence employed by the present invention for the quantitative measurement of fluid flow using a cylindrical NMR excitation pulse.
Figure 4:
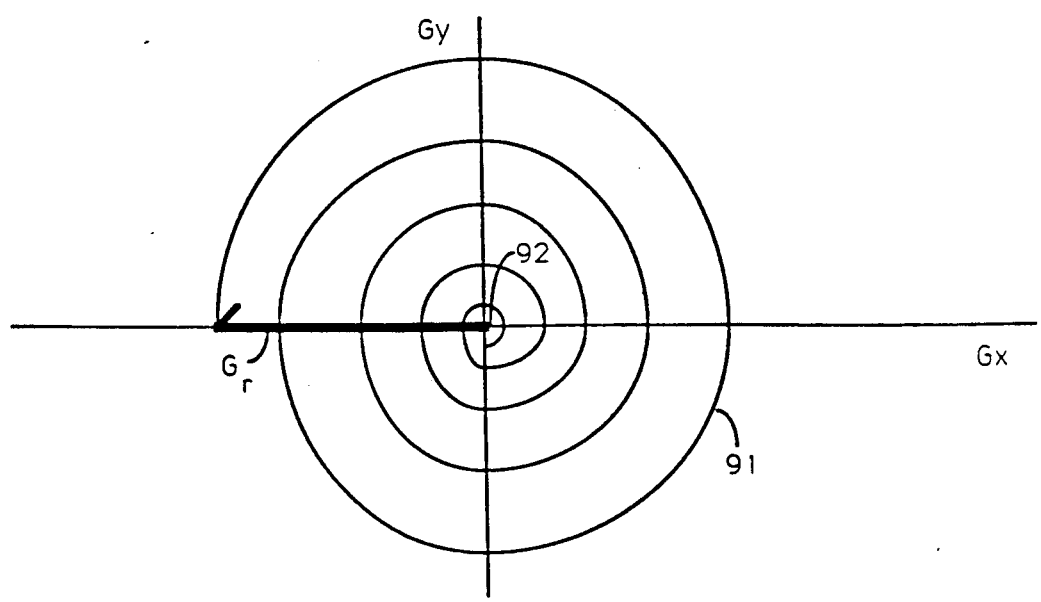
FIG. 4 is a graphical representation of the resultant Magnetic Gradient Vector change over time during cylindrical excitation.

Spatial localization in the present invention is achieved with rf pulses 62, 72 and gradient pulses 63, 73, 64, 74 of FIG. 3. The rf pulse 62 changes amplitude over time as the $G_x$ and $G_y$ orthogonal magnetic field gradients 63 and 64 create a resultant gradient field vector $G_r$ as shown in FIG. 4. The tip of vector $G_r$ traces a spiral. The $G_x$ and $G_y$ orthogonal gradient waveforms 63 and 64 and rf pulse 62 applied simultaneously, result in excitation of a cylindrical element of the subject. The prior art employs slab or slice excitation geometry for MR imaging. The rf pulse 62 of FIG. 3 is chosen to be the weighted two-dimensional Fourier transform of the desired excitation profile as disclosed by Pauly J, Nishimura D, Macovski A. "A K-Space Analysis of Small Tip-Angle Excitation" in *J. Magn. Reson.* 81:43, (1989). The spiral 91 of FIG. 4 can be traversed at a nonuniform rate to minimize pulse duration and double the bandwidth relative to a traversal at constant angular rate, under conditions of constrained gradient slew rate, consistent with the teachings of Hardy C. J., Cline H. E. "Broadband Nuclear Magnetic Resonance Pulses with Two-Dimensional Spatial Selectivity" in *J. Appl. Phys.* 66:1513, (1989). The rf waveform 62 is weighted by a factor which corrects for the nonuniform coverage of k-space by the spiral near the origin 92. A fuller discussion is given in Hardy C. J., Cline H. E., Bottomley P. A. "Correcting for Nonuniform K-Space Sampling in Two-Dimensional NMR Selective Excitation" in *J. Magn. Reson.* 87:639, (1990) hereby incorporated by reference and made part of this disclosure. This weighting removes baseline artifacts which can add contaminating signals from outside the central selected region to the excitation. Spiraltrajectory excitation pulses produce aliasing ring artifacts at radii determined by the length of the spiral 91 and the number of cycles in the spiral, as described by Hardy C. J., Cline HE. "Spatial Localization in Two Dimensions Using NMR Designer Pulses" in *J. Magn. Reson.* 82: 647, (1989) hereby incorporated by reference and made part of this disclosure. The rf pulse 62 of FIG. 3 was chosen to maximize the ratio between aliasing-ring radius (not shown) and excitation cylinder radius 85, shown in FIG. 5, without producing distortion of the profile or aliasing rings at the perimeter of the cylinder 81 (shown in FIG. 4), while exciting a Gaussian profile.

Figure 6A:
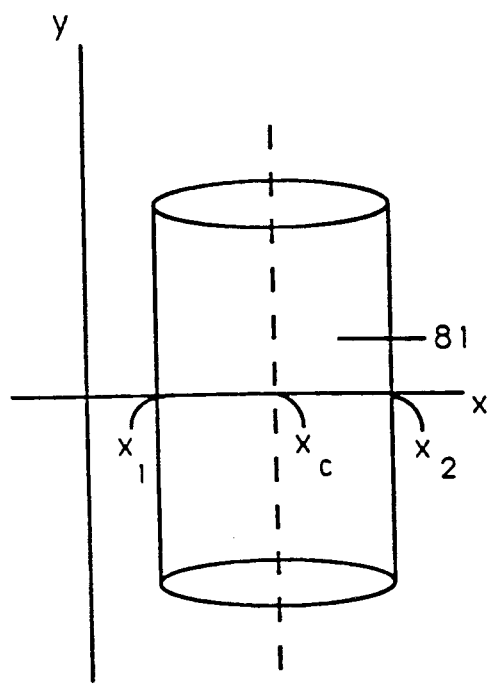
FIG. 6a and 6b show the transverse magnetization of the excitation cylinder after application of the excitation pulses.
Figure 6B:
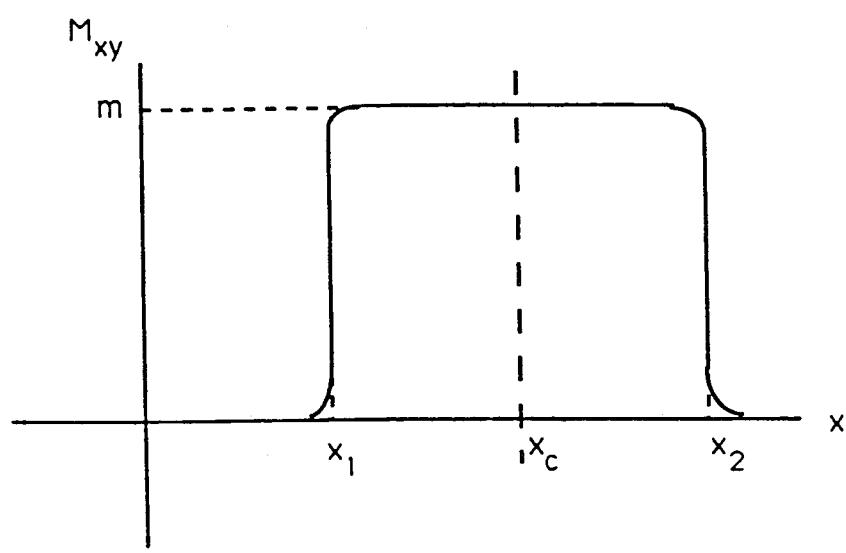

After application of the rf pulse 62 and magnetic gradients 63 and 64, shown in FIG. 3, excitation cylinder 81 has a transverse magnetization as indicated in FIGS. 6a and 6b. The center of cylinder 81 is at displacement $x_c$. At displacement $x_1$, shown in FIG. 6a, the transverse magnetization $M_{xy}$ is represented as $x_1$, as shown in FIG. 6b. The magnetization $M_{xy}$ remains substantially constant across the diameter of cylinder 81, having a magnetization amplitude m which drops off at radius $x_2$ of FIG. 6a, corresponding to point $x_2$ on the graph of FIG. 6b.

After the cylinder 81 is excited, it is then velocity encoded. The present invention utilizes Fourier velocity encoding with a pulse sequence 61 shown in FIG. 3.

Figure 2:
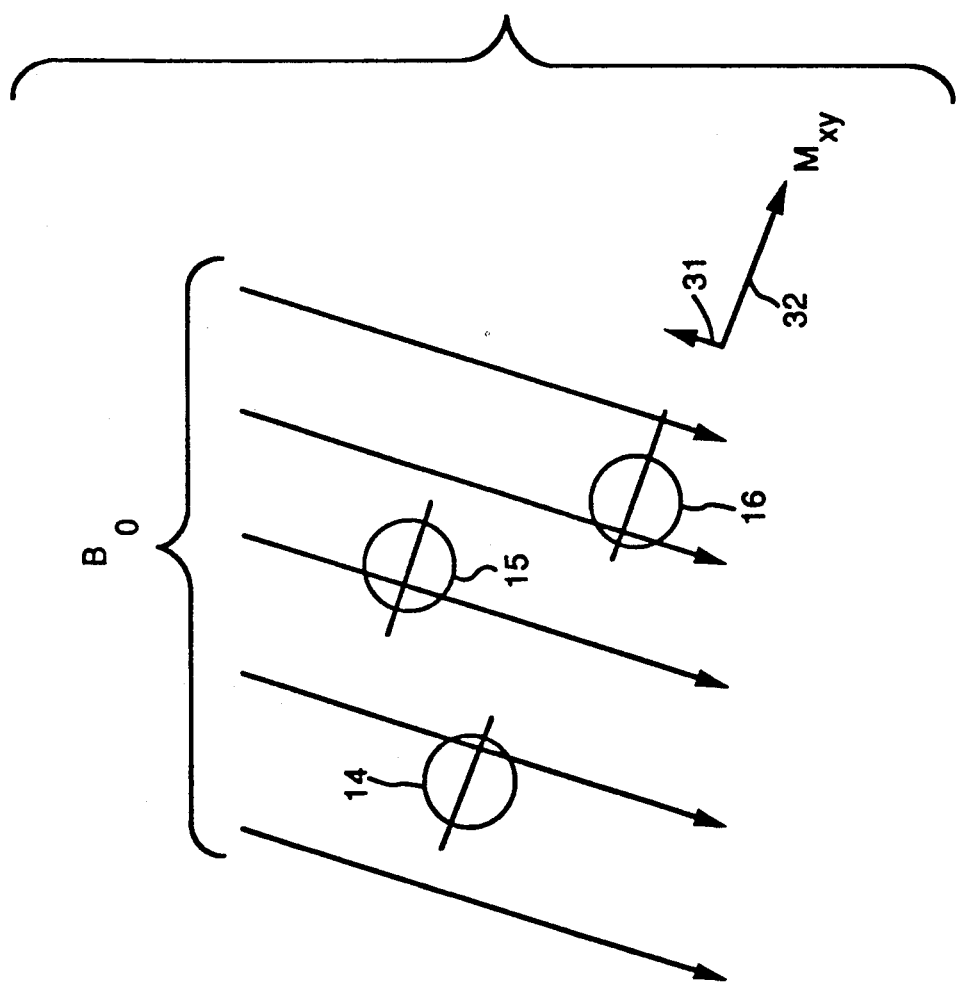
FIG. 2 is a representation of the spins of FIG. 1 after application of an NMR excitation pulse.

FIG. 7 is an amplitude vs. time diagram of a single component of the transverse magnetization vector 32 of FIG. 2 as it rotates at a given location in the sample.

The vector rotates at a specific constant frequency during period 54. Magnetic field gradient pulse 57 is applied during period 55, increasing the frequency or rate of change in phase of transverse magnetization 32 depending upon the area of gradient pulse 57. During period 56 of FIG. 7, the transverse magnetization reverts back to its original frequency, but the phase is increased, in this case, by 90 degrees. This is called phase evolution. It must be noted that if the polarity of gradient pulse 57 is reversed, it would cause a reverse effect on the phase shift, retarding the phase by 90 degrees.

The linear phase evolution of each spin 14, 15, 16 of FIGS. 2 is directly related to the position of the spin along the magnetic field gradient, the amplitude of the gradient applied to it, and the time during which it is applied (or the area under the gradient lobe 57). The phase shift of stationary spin is directly proportional to the lobe area 57.

Figure 8:
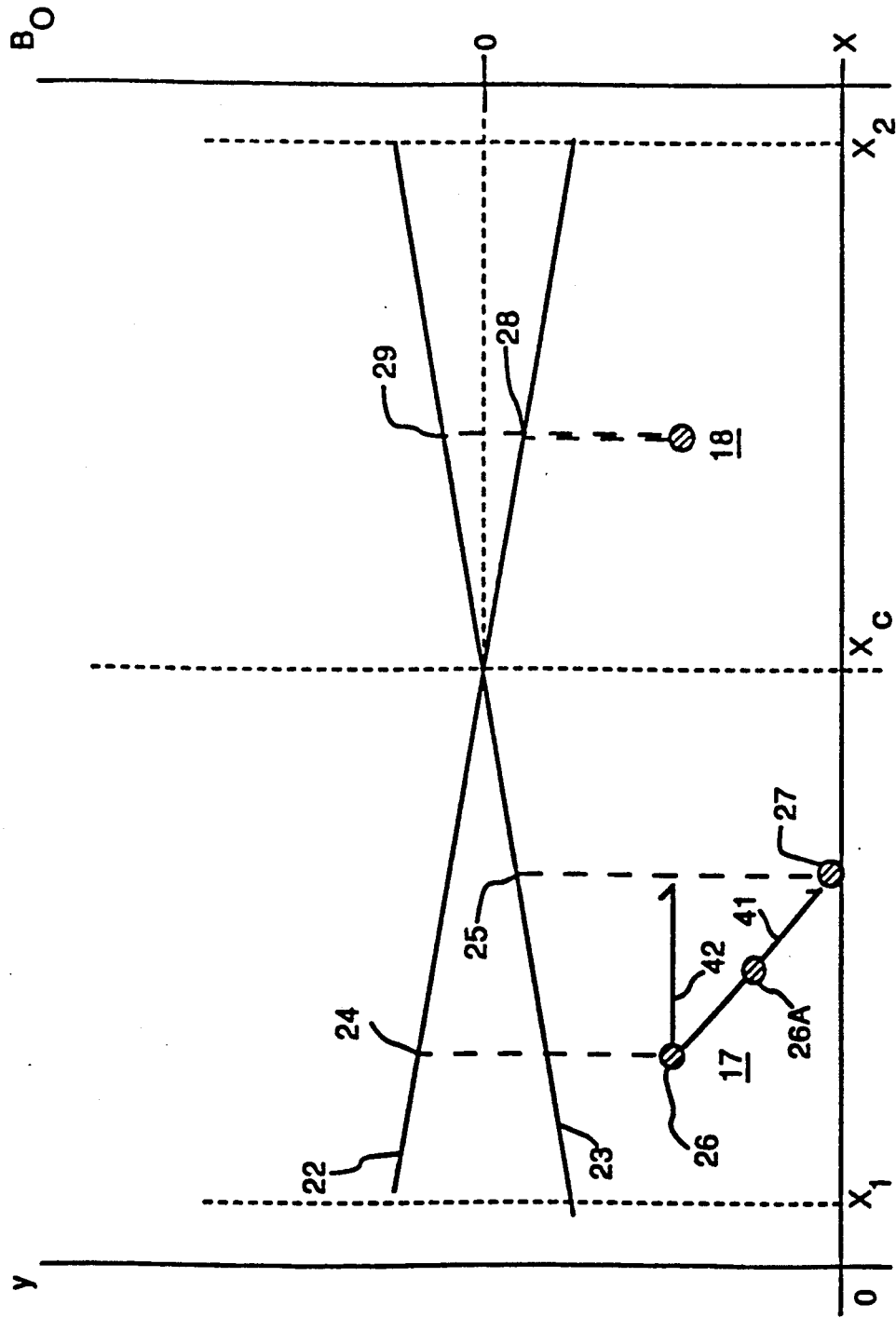
FIG. 8 is a graphical representation of the effect of two oppositely polarized magnetic gradients on spins.

FIG. 8 shows a spin 17 located at point 26 moving at a velocity 41 towards point 27. When spin 17 is at point 26 a negative gradient 22 is applied. When spin 17 is at point 26a a positive gradient 23 is applied. Over the entire period in which both gradients 22 and 23 are applied, spin 17 experiences phase evolution which arises from gradient 22 and gradient 23. The phase shift induced by gradient 23 is substantially opposite to that induced by gradient 22 because the gradient amplitude polarities 24 and 25 are substantially opposite, but are not exactly opposite due to the physical displacement of spin 17. The resultant phase shift arising from the application of the bipolar gradient comprised of gradients 22 and 23 is directly proportional to the velocity of spin 17. A spin moving in the opposite direction between points 27 and 26 will experience phase evolution which is exactly opposite that of spin 17.

A spin which is not moving in a direction along the gradient 22 or 23, such as spin 18, will first experience an negative gradient amplitude 28 followed by a positive gradient amplitude 29 of equal magnitude, the positive and negative amplitudes thereby cancelling each other out. FIG. 8 thus illustrates that the velocity of the spin 17 moving along a bipolar gradient 22 and 23 can be encoded by its phase evolution. FIG. 8 also shows that a spin 18 which does not have a velocity along the gradient will experience no additional phase evolution due to the bipolar magnetic field gradient.

Figure 9:
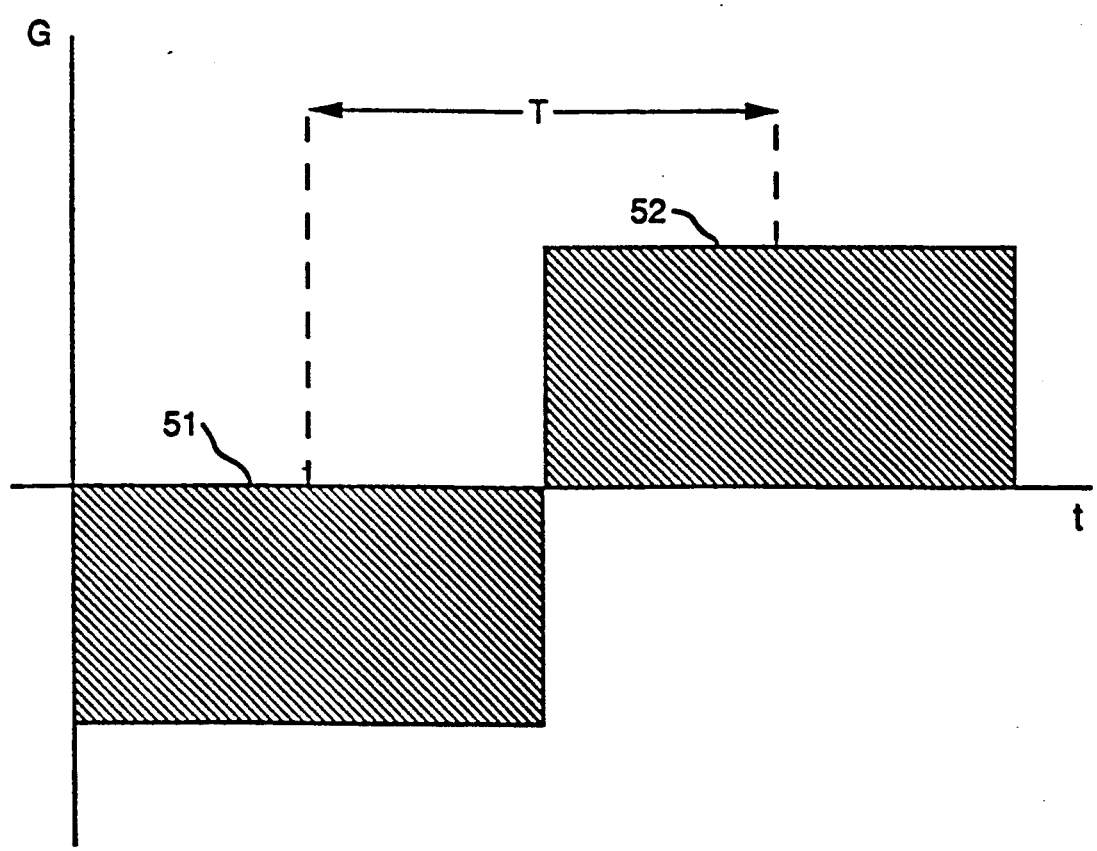
FIG. 9 is a graphical representation of amplitude versus duration of a flow encoding magnetic gradient pulse which may be used by the present invention for velocity encoding.

The phase shift induced by motion of transverse spin magnetization in the presence of a bipolar magnetic field gradient, $\phi(motion)$, can be described as:

$$\phi(motion) = \gamma \, VTA_g \quad [1]$$

where $\gamma$ is the gyromagnetic ratio specific to a given element, V is the component 42 of the spin's velocity 41 parallel to the direction of the gradient pulse, as shown in FIG. 8. T is shown in FIG. 9 as the time between the centers of the lobes of the magnetic gradient pulse applied along the line in which flow is to be measured, and $A_g$ is the area 51, 52 (gradient strength x duration of application) of one lobe of the bipolar pulse. Equation [1] ignores phase shifts which can arise from higher orders of motion such as acceleration and jerk.

Referring again to FIG. 5, in order to encode fluid flow, as represented by a vector 83, the present invention employs a flow encoding magnetic field gradient applied along a direction in which flow is intended to be measured, and represented by a vector 86. This causes phase evolution of the spins to occur, with the higher velocity spins evolving faster than the lower velocity spins. Using equation [1], the velocity 42 of a sample of spins 17 and 18, as represented in FIG. 8, can be quantitatively measured if the phase shift can be determined.

Unfortunately, MR signals from a spatial region come from an ensemble of spins and if these spins are moving, their velocity is characterized by a distribution, rather than a single velocity. This distribution can be broad enough to cause the phase of the component spin signals to cancel and thus result in a loss of signal.

One way to overcome the problem of spin velocities interfering with each other upon data acquisition is to convert one spatial dimension of a conventional image into a velocity dimension. This adds a dimension in which the velocity data (and its distribution) can be measured.

The present invention exploits the properties of the Fourier Transform to separate the constituent velocities on reconstruction and prevent signal loss. This is done by, for example, on a series of excitations applying successively a larger flow encoding gradients 51, 52, of FIG. 9, 61, 71 of FIG. 3 or larger separations T, as shown in FIG. 9, and sampling the re-radiated data. This allows data to be collected for a number of flow encoding gradient amplitudes. Fourier transformation is then used to separate the various velocity constituents by virtue of their modulation frequencies to produce a data vector which presents signal intensity as a function of velocity. It will be noted that the bipolar flow-encoded gradient wave forms 61, 71 of FIG. 3 are two of a series of wave forms each having a differing amplitude.

The present invention bears some similarity to the Fourier-encoded velocity measurements proposed by Feinberg et al. and Hennig et al., supra; however the pulse sequences utilized by the present invention differ from the pulse sequences of Feinberg et al. and Hennig et al. Cylindrical field excitation and independent flow encoding geometry are not employed by Feinberg et al. and Hennig et al.

Figure 5:
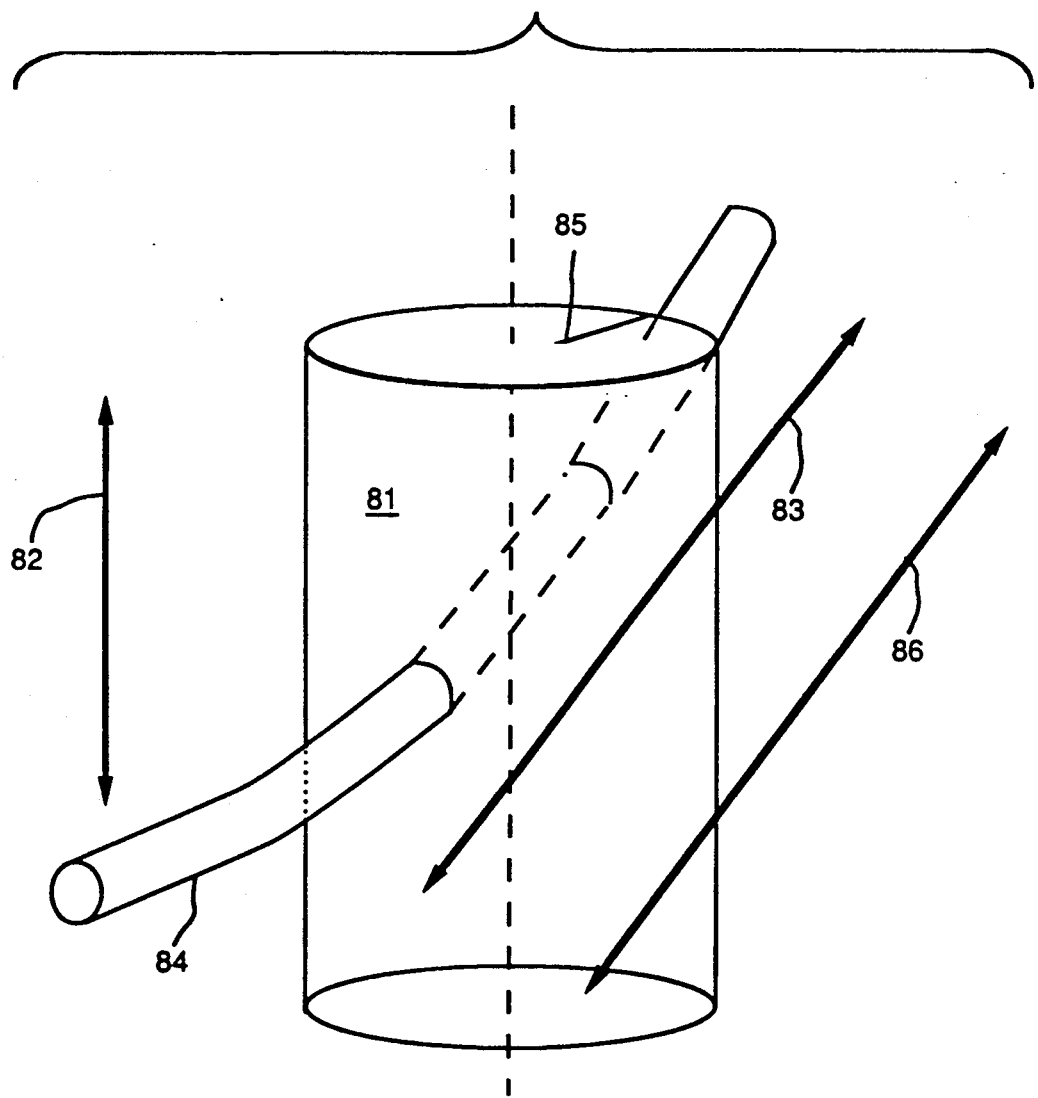
FIG. 5 shows the relative geometry of the area of cylindrical excitation, the flow encoding gradient, flow sensitivity, and the readout gradient.

Data are acquired by applying a readout magnetic field gradient 65, 75, as shown in FIG. 3 and represented by vector 82 of FIG. 5, parallel to the axis 122 of the excitation cylinder 81 of FIG. 5. The spins 17, 18 represented in FIG. 8, re-radiate photons when in the excited state and placed in a magnetic field gradient such as the readout gradient 65, 75, as represented by vector 82 of FIG. 5. Each readout gradient pulse 65, 75 has two lobes as shown in FIG. 3. The first lobe has an area 66, 76 equal to the first half 67, 77 of the second lobe. The readout gradient causes a negative phase evolution during application of the first lobe 66, 76, followed by a positive phase evolution during application of the first half 67, 77 of the second lobe, causing a rephasing at its midpoint 69, 79. The peak of the signal echo 101, 111 occurs at this point in time. This echo is a gradient recalled echo. Signals 101, 111, etc. are sensed and stored.

The resulting data set has a single spatial dimension (i.e. the readout dimension) and one velocity dimension which is sensitive only to the component of velocity which is parallel to the applied flow encoding magnetic field gradient pulse 42, shown in FIG. 8.

With respect to in FIG. 5, the relative orientations of the flow encoding gradient 85, readout gradient 82 and excitation cylinder 81 are not constrained, and can be orthogonal, parallel or oblique. The cylinder 81 can be reoriented by mixing the gradient $G_x$ waveforms 63, 73 and $G_y$ waveforms 64, 74 from FIG. 3 and offset from gradient isocenter by frequency modulating of the rf pulse 62 of FIG. 3.

The velocity resolution of the resulting flow measurement can be calculated by using the Nyquist criterion with equation [1]. The Nyquist criterion specifies that phase difference between adjacent samplings of a signal must be less than if the signal is not aliased. Consequently, the maximum phase shift which is obtained for the highest non-aliased velocity is $$\phi(max) = \pi V_{res}/2 \qquad [2]$$

where $V_{res}$ is the number of velocity encoded samples in a procedure in which the area of a flow encoding lobe 61, 71, as shown in FIG. 3, is varied from $A_{g\ (max)}$ to $-A_{g\ (max)}$. The velocity resolution, $V_{res}$, (cm/s/pixel) can then be determined by combining equations [1] and [2] to give:

$$V_{res} = \frac{1}{2\gamma T A_{g(max)}} \qquad [3]$$

The pulse sequence illustrated in FIG. 3 is very flexible and can be applied in a variety of manners. Since the orientation of the readout gradient 82, flow encoding gradient 86 and excitation cylinder 81, as shown in FIG. 5, are independent of one another, it is possible to optimize the pulse sequence for different vascular anatomies and applications. For example, the geometry shown in FIG. 5 can be modified such that the flow-encoding gradients are applied in three orthogonal directions in three successive scans. (See U.S. Pat. No. 4,796,635, Dumoulin, issued Jan. 10, 1989.) This triples the required scan time, but permits the quantification of blood flow without prior knowledge of the vessel geometry.

Since most of the blood flow in the body of most living subjects is pulsatile, it is frequently useful to repeat the pulse sequence for several time frames after the detection of an r-wave of a cardiac cycle to provide a temporal dimension for the data.

Synchronization of acquisition with the cardiac cycle is essential if the temporal characteristics of blood flow are to be measured. Velocity measurements performed with cardiac gating are made synchronously over a large number of cardiac cycles and permit the differentiation of constant and periodic flow. Under these conditions, both periodic and constant flow behavior are easily measured and the velocity distribution is well characterized (i.e. there is little signal intensity at unexpected velocities).

Figure 10:
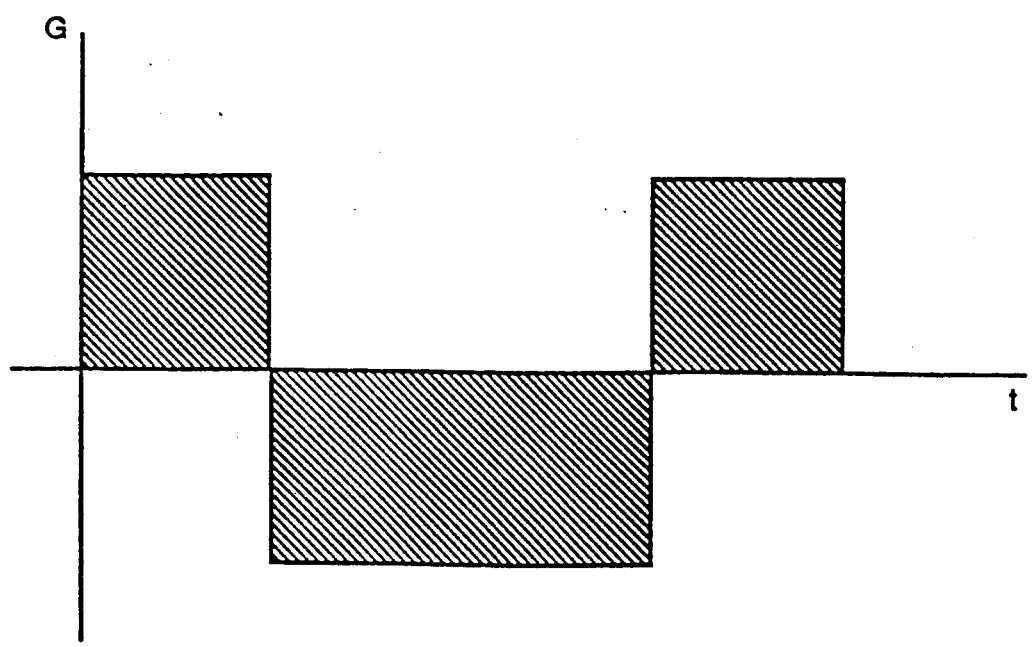
FIG. 10 is a graphical representation of amplitude versus duration of a flow encoding magnetic gradient pulse which may be used by the present invention for acceleration encoding.

Another variation of the sequence that may be employed in the present invention is the conversion of the bipolar flow-encoding pulse into a three-lobed acceleration encoding pulse as shown in FIG. 10 or a three-lobed acceleration compensated/velocity encoding pulse. See Dumoulin C. L., Souza S. P., Walker M. F. and Yoshitome E. "Time-resolved Magnetic Resonance Angiography", *Mag. Reson. Med.* 6:275, (1988) hereby incorporated by reference and made part of this disclosure. The application of Fourier acceleration encoding to in-vivo systems, however, is limited by the strength of the gradient subsystem in currently available instruments, with maximum gradient amplitudes on the order of 1 G/cm. Use of a three-lobed acceleration pulse would result in suppression of any differential orders of motion below the second differential order of motion, which is useful in imaging acceleration of fluids. In other words, non-moving spins and spins moving with constant velocity would be suppressed.

Figure 11:
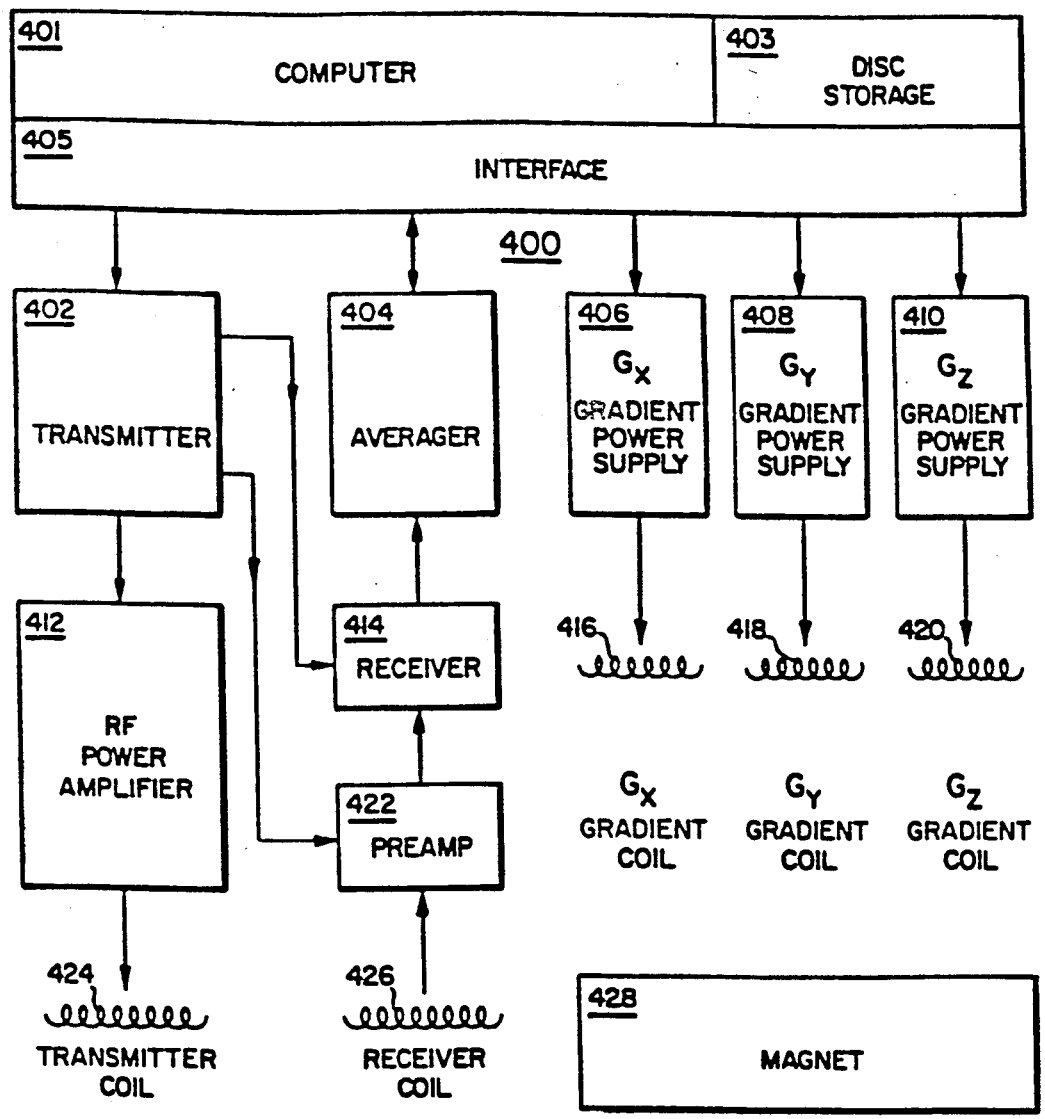
FIG. 11 is a simplified block diagram of the major components of an NMR imaging apparatus suitable for producing pulse sequences shown in FIG. 3.

FIG. 11 is a simplified block diagram of the major components of an NMR imaging system suitable for use with the NMR pulse sequences of the invention described herein. The system, generally designated 400, is made up of a general purpose mini-computer 401 which is functionally coupled to disk storage unit 403 and an interface unit 405. An RF transmitter 402, signal averager 404, and gradient power supplies 406, 408 and 410 for energizing, respectively, x, y, z gradient coils 416, 418, and 420 are coupled to computer 401 through interface unit 405.

RF transmitter 402 is gated with pulse envelopes from computer 401 to generate RF pulses having the required modulation to excite nuclear resonance in the subject under study. The RF pulses are amplified in RF power amplifier 412 to levels varying from 100 watts to several kilowatts, depending on the imaging method, and applied to transmitter coil 424. The higher power levels are necessary for large sample volumes such as in whole body imaging, and where short duration pulses are required to excite large NMR frequency bandwidths.

The NMR signal is sensed by receiver coil 426, amplified in a low noise preamplifier 422, and applied for further amplification, detection, and filtering to receiver 414. The signal is then digitized for averaging by signal averager 404 and for precessing by computer 401. Preamplifier 422 and receiver 414 are protected from the RF pulses during transmission by active gating or by passive filtering.

Computer 401 provides gating and envelope modulation for the NMR pulses, blanking for the preamplifier and RF power amplifier, and voltage waveforms for the gradient power supplies. The computer also performs data processing such as Fourier transforms, image reconstruction, data filtering, imaging display, and storage functions (all of which are beyond the scope of the present invention).

Figure 12:
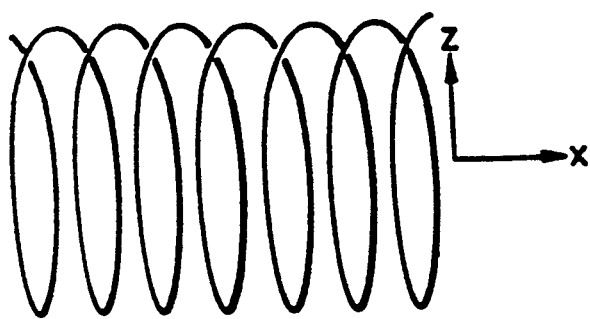
FIG. 12 illustrates an rf coil design for use with geometries for which a sample chamber is perpendicular to the static magnetic field $B_0$.
Figure 13:
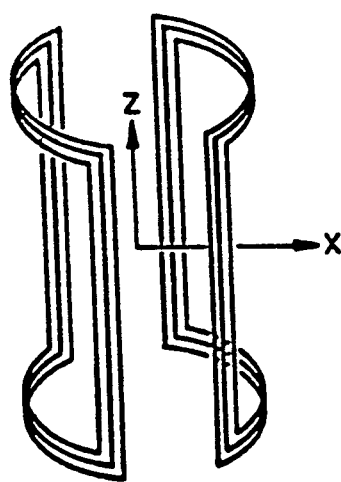
FIGS. 13 and 14 illustrate rf coil designs for use with geometries for which a sample chamber is parallel to the static magnetic field $B_0$.
Figure 14:
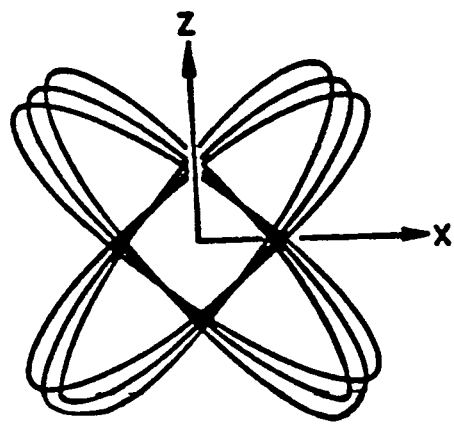

The transmitter and receiver RF coils, if desired, may comprise a single coil. Alternatively, two separate coils that are electrically orthogonal may be used. The latter configuration has the advantage of reduced RF pulse breakthrough into the receiver during pulse transmission. In both cases, the coils are orthogonal to the direction of the static magnetic field $B_o$ produced by magnet 428 (FIG. 11). The coils are isolated from the remainder of the system by enclosure in an RF shielded cage. Three typical RF coil designs are illustrated in FIGS. 12, 13, and 14. All of these coils produce RF magnetic fields in the x direction. The coil designs illustrated in FIGS. 13 and 14 are suitable for magnetic geometries for which the axis of the sample chamber is parallel to the main field $B_o$ (FIG. 1) The design illustrated in FIG. 12 is applicable to geometries for which the sample chamber axis is perpendicular to the main field $B_o$ (not shown).

Magnetic field gradient coils 416, 418, and 420 (FIG. 11) are necessary to provide gradients $G_x$, $G_y$, and $G_z$, respectively. In the imaging pulse sequences described herein, the gradients should be monotonic and linear over the sample volume. Multivalued gradient fields cause a degradation in the NMR signal data, known as aliasing, which leads to severe image artifacts. Nonlinear gradients cause geometric distortions of the image.

An example of use of the present invention for the quantitative measurement of blood flow in the portal vein of a human subject is disclosed here. The relationship between the readout gradient 82, excitation cylinder 81 of the human subject and flow encoding gradient 86 directions is illustrated in FIG. 5.

Data were acquired on 1.5 Tesla imaging systems (General Electric Company, Milwaukee, WI) with shielded gradient coil subsystem. Velocity quantification was performed using the pulse sequence outlined above. Unless stated otherwise, TR=44.0 ms, TE=28.8 ms, rf flip angle=20 degrees, NEX=1, and the acquisition matrix was 256×256. Twenty velocity samples per cardiac cycle were typically obtained in gated studies. The strength of the flow encoding gradient was calculated to provide a velocity resolution of 2.0 cm/s/pixel. The diameter of the cylindrical excitation was 2 cm. The k-space spiral had 8 complete turns, a radius of 2.1 radians/cm and a pulse duration of 10.0 ms.

Figure 15:
FIG. 15 is an MR image of a human abdomen used to localize vessels in which fluid flow is to be measured by the present invention.
Figure 16:
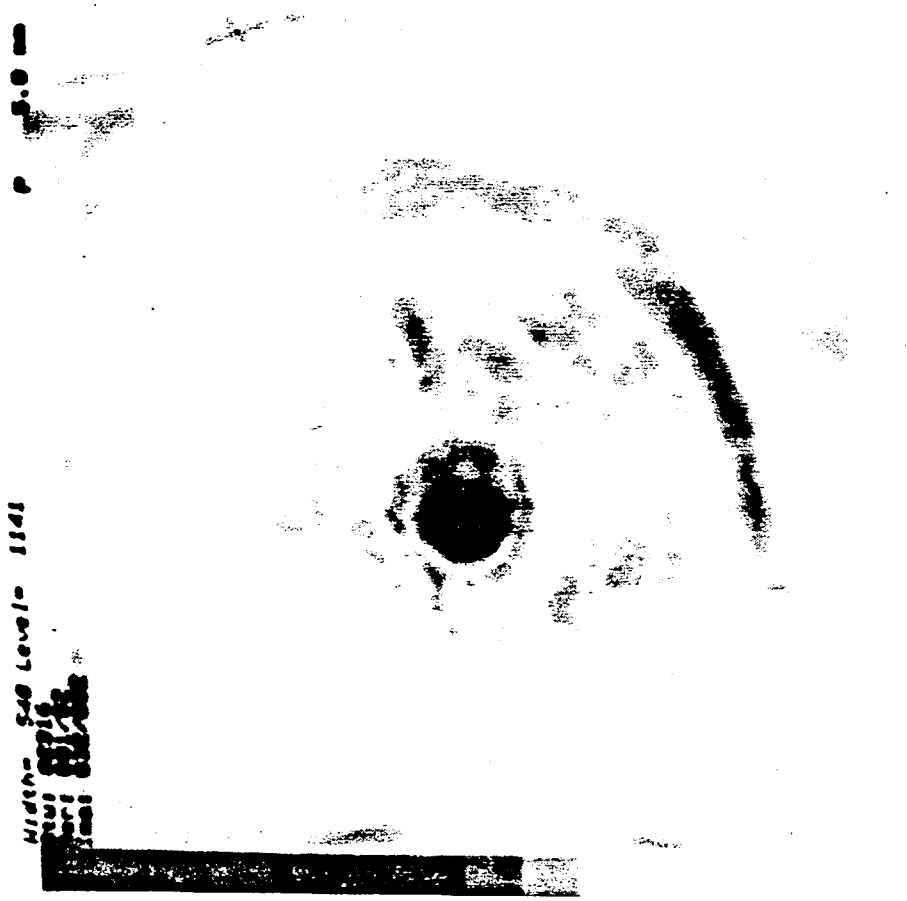
FIG. 16 shows a coronal MR image acquired with an A/P cylindrical excitation pulse to verify the placement of the excitation.

In order to perform the scan, each subject's abdomen was compressed with a wide strap. Subjects were instructed to exhale and then hold their breath during the non-cardiac gated scans but were allowed to breath normally during the gated acquisitions. A 128×256 localization scan was performed first to determine the approximate location and orientation of the portal vein. The localization scan employed could be a multiple slice gradient recalled echo sequence which is fast enough to permit the acquisition of at least 6 coronal images in a single 20 second breath hold. The localizer image, FIG. 15, was then examined and the displacement (with respect to the center of the magnet) of the portal vein was determined. The rf waveform 62 (FIG. 3) of the cylindrical excitation pulse was then modulated, as described in Pauly, Nishimura, Macovski (above) and also in Hardy C. J., Bottomley P. A., Roemer P. B., "Off-Axis Spatial Localization with Frequency Modulated Nuclear Magnetic Resonance Rotating $\rho$ Pulses", in *Journal of Applied Physics* 3:4741, (1988), to translate the excitation region to the location of the portal vein. A gradient recalled echo image using the offset cylindrical excitation was then collected and is shown in FIG. 16.

Figure 17:
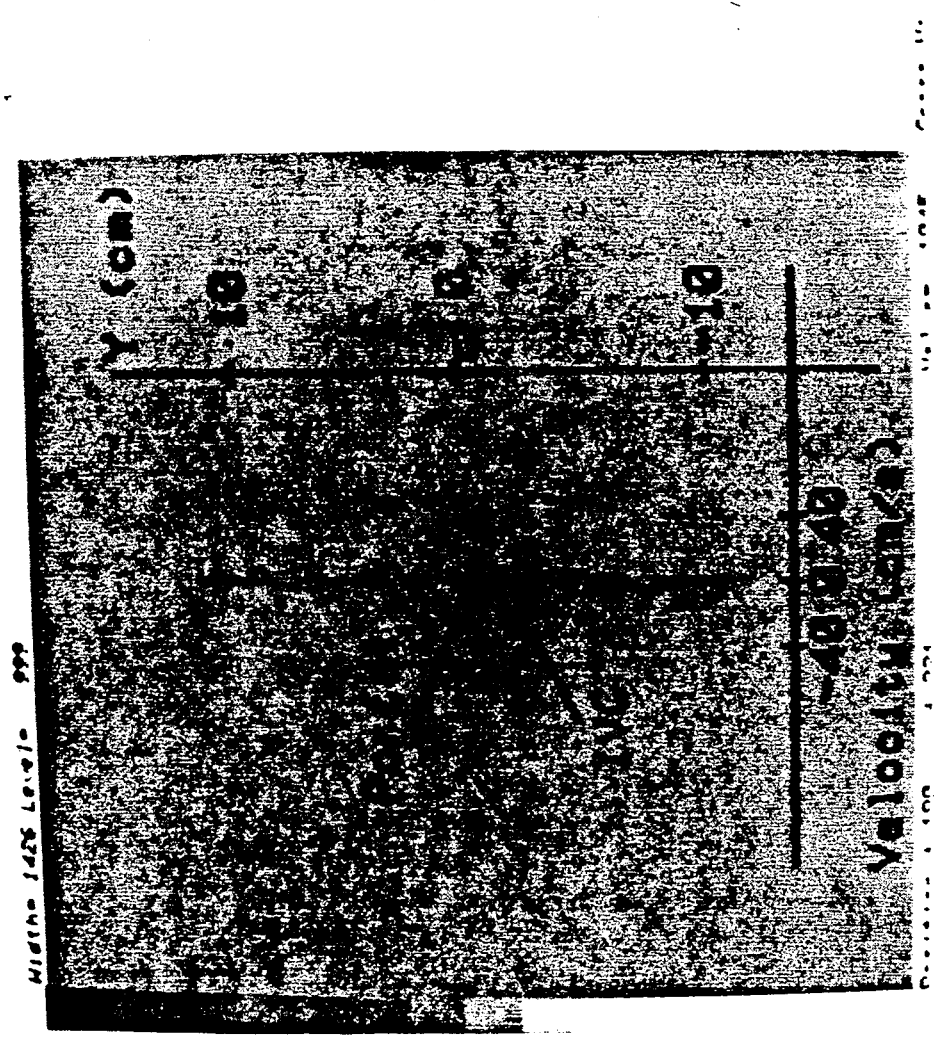
FIG. 17 shows a quantitative velocity image created by the use of the present invention in which the horizontal axis is in velocity units and the vertical axis represents spatial displacement of the measured flow along the Anterior Posterior direction.

The Fourier flow encoding procedure was then applied using the same cylindrical excitation geometry. Data were acquired in a single breath-hold with flow encoding gradients 61, 71 (FIG. 3) applied parallel to the portal vein. The resultant image is shown in FIG. 17. It will be noted that the Inferior Vena Cava (IVC) and the portal vein both have a negative velocity, indicating the direction of flow.

Figure 18:
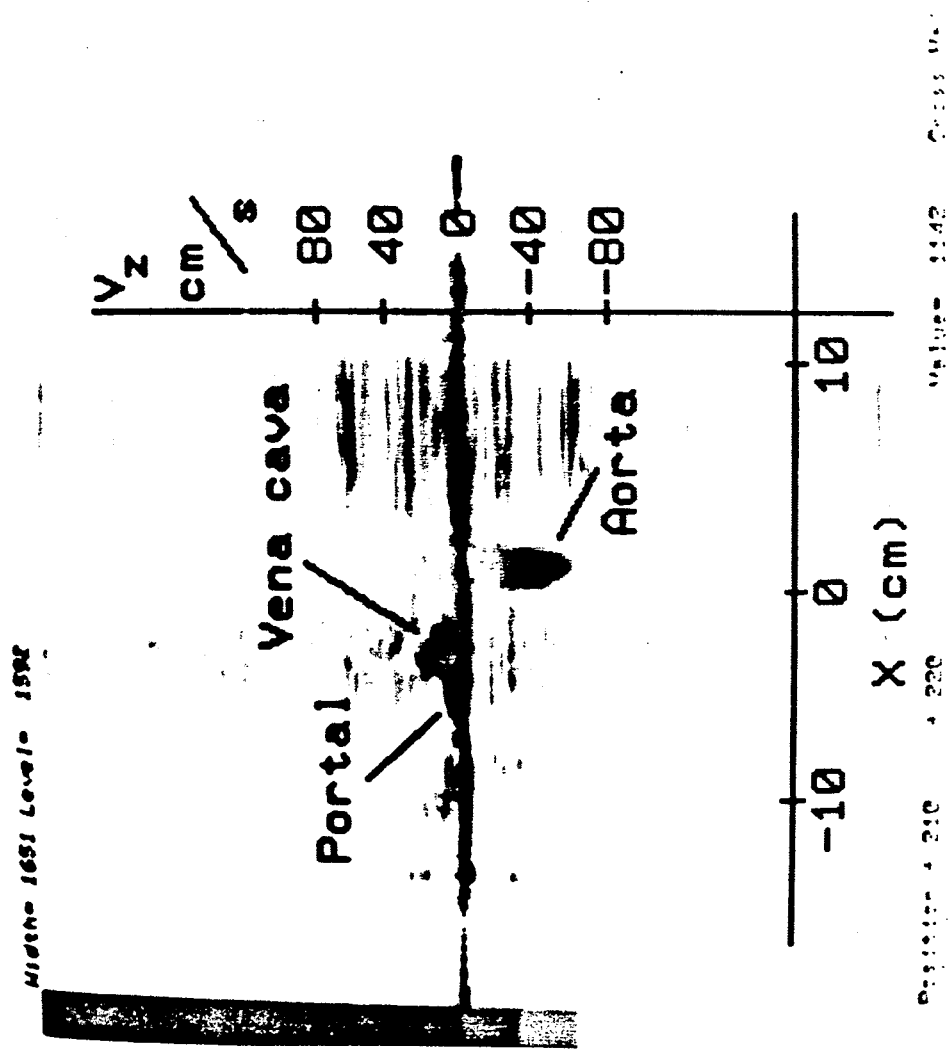
FIG. 18 is a velocity profile image of the aorta portal vein, and vena cava of a human abdomen at a selected phase of the cardiac cycle, created by the use of the present invention.

Taking a view along the axis X, perpendicular to the Y axis of FIG. 17, a velocity $V_z$ vs. displacement X plot can be constructed as shown in FIG. 18.

Figure 19:
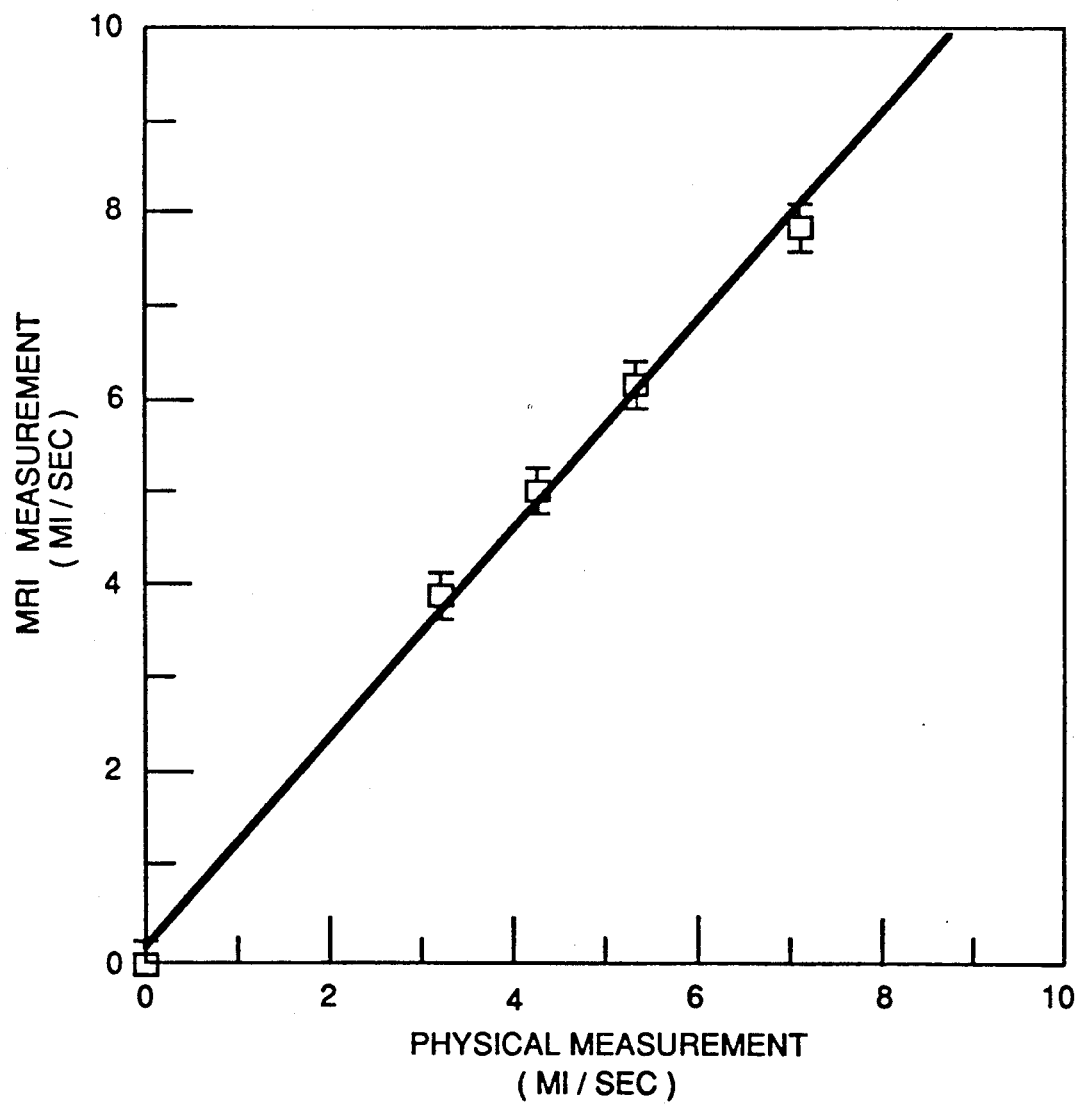
FIG. 19 is a graph of the correlation between flow measurements collected with the use of the present invention vs. physically measured fluid flow.

In order to determine the accuracy of blood flow measurements obtained by use of the present invention, a phantom study using water was performed. Data were collected for several flow rates and the flow measurements obtained with Fourier flow encoding ("MRI Measurement") in accordance with the present invention were compared to those obtained with a graduated cylinder apparatus and a stop watch ("Physical Measurement"). The correlation of the two measurements is shown in FIG. 19. The correlation coefficient was found to be 0.996. The flow measurements disclosed here are superior to measurements available today in radiological practice.

Fourier velocity encoded images such as those presented here can be used to measure several hemodynamic properties of blood flow. For example, the maximum velocity within a vessel is easily determined by finding the pixel within the limits of the vessel which has the greatest displacement in the velocity dimension. Since the intensity of each pixel in a velocity image is proportional to the number of spins moving at a given velocity and in a given location, the mean velocity and the width of the velocity distribution can be easily determined. This can be done for each point in the spatially encoded dimension or over the entire vessel. The width of the vessel can be determined in the readout direction, but if its cross section is noncircular or if the readout gradient is applied obliquely, a conventional image may be required for the determination of vessel cross-section. Once the cross sectional area is known, the total flow in the vessel can easily be determined.

Therefore, the present invention provides a method of NMR imaging of molecules having motion, while suppressing images of molecules having no motion. The present invention can also suppress images of molecules in motion described by first order differentials or images of molecules which are not moving while imaging molecules described by second order differentials of motion and high order differentials of motion.

While only certain preferred features of the invention have been illustrated and described herein, many modifications and changes will occur to those skilled in the art. It is, therefore, to be understood that the appended claims are intended to cover all such modifications and changes as fall within the true spirit of the invention.

We claim:

1. A method for quantitative measurement of fluid flow through a vessel of a subject comprising the steps of:

a) applying a homogeneous magnetic field over said subject;

b) performing a plurality of scans of said subject to acquire a set of scan data, each scan comprising the steps of:

applying a cylindrical excitation to a portion of said subject, flow encoding the excited portion of the subject by applying a flow encoding magnetic gradient pulse along an axis of the flow to be measured, the flow encoding magnetic gradient pulse having a predetermined amplitude varied from a positive maximum for an initial scan, to a negative maximum for the final scan, or a negative maximum for an initial scan, to a positive maximum for the final scan, and having at least one negative lobe and at least one positive lobe, collecting a set of scan data by
   applying to said subject a first readout magnetic field gradient pulse,
   applying to said subject a second readout magnetic field gradient pulse having an area under its amplitude vs. time curve greater than or equal to that of the first readout gradient field pulse but of opposite polarity,
   sensing an amount of MR signal re-radiated by the excited portion of said subject over a given period in the presence of the magnetic readout gradient field pulses, and
   storing the set of scan data related to the MR signal re-radiated by the subject pertaining to the corresponding predetermined amplitude of the flow encoding magnetic gradient pulse;

c) and reconstructing the scan data to determine said fluid flow by:
   two dimensionally Fourier transforming the scan data to reconstruct a fluid flow profile,
   determining a cross sectional diameter of said vessel from the scan data,
   calculating said fluid flow from the cross sectional diameter and the fluid flow profile.

2. A method for quantitative measurement of fluid flow in a subject as recited in claim 1 wherein the step of applying a cylindrical excitation comprises steps of:
   applying two simultaneous mutually orthogonal time changing magnetic field gradients to said subject such that the gradients create a resultant gradient vector that traces out a spiral shape in k space; and
   applying an rf excitation pulse to said subject, the rf pulse having an amplitude and duration corresponding to the orthogonal time changing magnetic fields such as to cause magnetic resonance or excitation of predetermined nuclei in the portion of said subject.

3. A method for quantitative measurement of fluid flow in a subject as recited in claim 2 further comprising a step of determining a location of said subject to be measured with the use of conventional Magnetic Resonance Imaging techniques, then confining the cylindrical excitation to said location to obtain an improved measurement.

4. A method for quantitative measurement of fluid flow in a subject as recited in claim 2 wherein the flow encoding magnetic gradient pulse has three lobes such that the area under a time vs. amplitude curve of the first lobe and the third lobe is equal to the second lobe, and the area under an amplitude vs. duration curve of the second lobe is the negative of the total area under an amplitude vs. duration curve of the first and third lobes, so as to encode fluid flow in the excited portion of said subject having motion along the direction of the flow encoding magnetic gradient, the motion of said fluid being described by first order of higher differentials of velocity with respect to time.

5. A method for quantitative measurement of fluid flow in a subject as recited in claim 2 further comprising a step of applying, after the set of applying cylindrical excitation, and before the step of collecting the scan data, an rf pulse of a predetermined amplitude to the excited portion to cause a 180 degree rotation of spins relative to their positions before application of the rf pulse in order to cancel errors incurred by magnetic field homogeneity.

6. A method for quantitative measurement of fluid flow in a subject as recited in claim 2 further comprising a step of applying an rf pulse of a predetermined amplitudes and a gradient pulse of a predetermined amplitude to cause spins in a selected region to become saturated and thereby not contribute to the observed signal.

7. A method for quantitative measurement of fluid flow in a subject as recited in claim 2 wherein the rf excitation pulse and the two mutually orthogonal gradient filed pulses are chosen to excite a volume of arbitrary shape in two-dimensions and infinite extent in the third dimension.

8. A method for quantitative measurement of fluid flow in a subject as recited in claim 7 in which the rf pulse and the two mutually orthogonal gradient field pulses and a third mutually orthogonal gradient field pulse are chosen to excite a volume of arbitrary shape in three dimensions.

9. A method for quantitative measurement of fluid flow in a subject as recited in claim 1 wherein the flow encoding magnetic gradient pulse has only two lobes, the first flow encoding magnetic gradient pulse lobe having a predetermined amplitude varied from a positive maximum for an initial scan, to a negative maximum for the final scan, or a negative maximum for an initial scan, to a positive maximum for the final scan, and the second flow encoding magnetic gradient pulse lobe having opposite magnitude and the same area under its amplitude vs. duration curve as the first lobe, the flow encoding magnetic gradient causing encoding of said fluid having motion described by first order differentials or higher in the excited portion of the subject.

10. A method for quantitative measurement of fluid flow in a subject as recited in claim 9 wherein the plurality of scans are timed to correspond to a specific point of a cardiac cycle of the subject in order to create an instantaneous velocity profile.

11. A method for quantitative measurement of fluid flow in a subject as recited in claim 10 including a step of reconstructing, from the set of scan data collected from said scans, instantaneous flow images corresponding to the specific point of the cardiac cycle.

12. A method for quantitative measurement of fluid flow in a subject as recited in claim 11 including a step of displaying the instantaneous flow images in sequence to create a motion picture of the flow images.

* * * * *

UNITED STATES PATENT AND TRADEMARK OFFICE
CERTIFICATE OF CORRECTION

PATENT NO. : 5,133,357

DATED : July 28, 1992

INVENTOR(S) : Charles L. Dumoulin, et al

It is certified that error appears in the above-identified patent and that said Letters Patent is hereby corrected as shown below:

TITLE PAGE, ITEM [75], INVENTOR'S NAME IS MISSPELLED

PLEASE DELETE "SUZA" AND SUBSTITUTE ----SOUZA----

Signed and Sealed this

Thirty-first Day of August, 1993

*Attest:*

BRUCE LEHMAN

*Attesting Officer*     Commissioner of Patents and Trademarks